US009155687B2

(12) United States Patent
Beckman et al.

(10) Patent No.: US 9,155,687 B2
(45) Date of Patent: *Oct. 13, 2015

(54) ULTRA-VIOLET RADIATION ABSORBING SILICON PARTICLE NANOCLUSTERS

(71) Applicants: James Beckman, Springdale, AR (US); Anatoli Ischenko, Moscow (RU)

(72) Inventors: James Beckman, Springdale, AR (US); Anatoli Ischenko, Moscow (RU)

(*) Notice: Subject to any disclaimer, the term of this patent is extended or adjusted under 35 U.S.C. 154(b) by 49 days.

This patent is subject to a terminal disclaimer.

(21) Appl. No.: 13/762,796

(22) Filed: Feb. 8, 2013

(65) Prior Publication Data

US 2014/0037702 A1 Feb. 6, 2014

Related U.S. Application Data

(63) Continuation-in-part of application No. 12/928,093, filed on Dec. 3, 2010, now Pat. No. 8,394,412, which is a continuation-in-part of application No. 11/588,105, filed on Oct. 26, 2006, now Pat. No. 8,679,538, application No. 13/762,796, which is a continuation-in-part of application No. 12/291,973, filed on Nov. 13, 2008, now Pat. No. 7,624,883, and a continuation-in-part of application No. 12/291,973, filed on Nov. 13, 2008, now Pat. No. 7,624,883, said application No. 11/588,105 is a continuation-in-part of application No. 11/094,837, filed on Mar. 30, 2005, now abandoned.

(60) Provisional application No. 60/730,271, filed on Oct. 26, 2005, provisional application No. 60/558,209, filed on Mar. 30, 2004.

(51) Int. Cl.
| | |
|---|---|
| A61K 8/02 | (2006.01) |
| A61Q 17/00 | (2006.01) |
| A61K 8/25 | (2006.01) |
| A61Q 17/04 | (2006.01) |
| B82Y 5/00 | (2011.01) |
| B82Y 30/00 | (2011.01) |
| B82Y 20/00 | (2011.01) |

(52) U.S. Cl.
CPC .............. *A61K 8/0245* (2013.01); *A61K 8/0241* (2013.01); *A61K 8/25* (2013.01); *A61Q 17/00* (2013.01); *A61Q 17/04* (2013.01); *B82Y 5/00* (2013.01); *A61K 2800/413* (2013.01); *A61K 2800/621* (2013.01); *B82Y 20/00* (2013.01); *B82Y 30/00* (2013.01); *Y10S 977/773* (2013.01)

(58) Field of Classification Search
None
See application file for complete search history.

(56) References Cited

U.S. PATENT DOCUMENTS

| 5,637,258 A | 6/1997 | Goldburt et al. ........... 252/301.4 |
| 5,852,346 A | 12/1998 | Komoda et al. ............ 315/169.3 |

(Continued)

OTHER PUBLICATIONS

A.I. Belogorokhov, R. Enderlein, A. TAbata, J.R. Leite, V.A. Karavanskii, L.I. Belogorokhova, Enhanced photoluminescence from porous silicon formed by non-standard preparation, Physical Review (B), 56 10276-10282 (1997).

(Continued)

*Primary Examiner* — Isaac Shomer
(74) *Attorney, Agent, or Firm* — Keisling & Pieper PLC; David B. Pieper

(57) ABSTRACT

Silicon particle nano-clusters formed with crystalline cores and amorphous shells are used for absorbing ultraviolet wavelength radiation. Silicon nano-particles are synthesized by plasma-chemical sputtering of bulk silicon crystal to form particles which are then quenched in an atmosphere of oxygen or oxygen and nitrogen. Analysis of these particles is presented for their scattering and absorption properties for use as ultraviolet protection elements.

15 Claims, 13 Drawing Sheets

(56) References Cited

U.S. PATENT DOCUMENTS

| | | | |
|---|---|---|---|
| 5,962,132 | A | 10/1999 | Chang et al. ............... 428/402 |
| 6,268,041 | B1 | 7/2001 | Goldstein ................... 428/208 |
| 6,471,930 | B2 | 10/2002 | Kambe et al. ............... 423/335 |
| 6,585,947 | B1 | 7/2003 | Nayfeh et al. .............. 423/348 |
| 6,846,565 | B2 | 1/2005 | Korgel et al. ............... 428/402 |
| 6,961,499 | B2 | 11/2005 | Lee et al. ................... 385/122 |
| 6,992,298 | B2 | 1/2006 | Nayfeh et al. .............. 250/372 |
| 7,005,669 | B1 | 2/2006 | Lee .............................. 257/21 |
| 7,020,372 | B2 | 3/2006 | Lee et al. ................... 385/129 |
| 7,078,276 | B1 | 7/2006 | Zurcher et al. ............. 438/151 |
| 8,394,412 | B1 * | 3/2013 | Beckman et al. ........... 424/489 |
| 8,679,538 | B2 * | 3/2014 | Beckman et al. ........... 424/489 |
| 2003/0003300 | A1 * | 1/2003 | Korgel et al. ............... 428/402 |
| 2004/0105980 | A1 | 6/2004 | Sudarshan et al. .......... 428/404 |

OTHER PUBLICATIONS

A.I. Belogorohov, L.I. Belogorohova, Optical properties of layers of the porous silicon received with use of electrolit ICl: HF: C2H5OH, FTP, 33 198-205 (1999).

A.I. Belogorokhov, Yu. A. Pusep, L.I. Belogorokhova, FTIR—study of the topology of porous semiconductor structures, Journal of Physics: Condensed Matter, 12 3897-3899 (2000).

D. Stryahuev, F. Diehlo, B. Schroder, M. Scheib, A.I. Belogorokhov, On the splitting of SiH absorption bands in infrared spectra of hydrogenated microcrystalline silicon, Philosophical Magazine B, 80 1799-1810 (2000).

T. Matsumoto, A.I. Belogorokhov, L.I. Belogorokhova, Y. Masumoto, E.A. Zhukov, The effect of deuterium on the optical properties of free-standing porous silicon layers, Journal of Nanotechnology, 11 340-347 (2000).

Gavrilov S.A., Belogorohov A.I., Belogorohova L.I., the Mechanism of oxygen passivation of porous silicon in solutions HF: HCl: C2H5OH, FTP, 36 104-108 (2002).

L.I. Belogorokhova, A.I. Belogorokhov, S.A. Gavrilov, V.Yu. Timoshenko, P.K. Kashkarov, M.G. Lisachenko, and S.P. Kobeleva, Enhanced photoluminescence and structural properties of porous silicon formed in hydrofluoric-hydrochloric solutions, Physica Status Solidi (a), 197 228-231 (2003).

I.A. Tutorsky, G.A. Grigoriev, G.A. Simakova, Dynamic processes on liquid interphase borders at synthesis of polymers and particles. In book <<Structurization and the interphase phenomena in systems a liquid-liquid, 1., RHTU, 2001, pp. 106-124.

D.A. Zimnyakov, D.N. Agafonov, A.P. Sviridov, L.V. Omelchenko, V.N. Kuznetsova, V.N. Bagratashvili, Speckle-contrast monitoring of tissue thermal modification, Applied Optics, 41, 5984-5988 (2002).

Scheer et al. (Journal of Applied Physics, vol. 93, No. 9, May 1, 2003, 99.5637-5642.

* cited by examiner

ULTRA-VIOLET RADIATION ABSORBING SILICON PARTICLE NANOCLUSTERS

CROSS-REFERENCE TO RELATED APPLICATIONS

This application claims priority to and is a continuation of U.S. application Ser. No. 12/928,093 filed on Dec. 3, 2010, which claims priority to and is a continuation-in-part of U.S. application Ser. No. 11/588,105 filed on Oct. 26, 2006, which claims priority to and is a continuation-in-part of U.S. provisional application Ser. No. 60/730,271 filed on Oct. 26, 2005; and is a continuation-in-part of U.S. application Ser. No. 12/291,793 filed on Nov. 13, 2008, which is a continuation of and claims priority to U.S. application Ser. No. 11/094,837 filed on Mar. 30, 2005, which is a continuation-in-part of U.S. provisional application Ser. No. 60/558,209 filed on Mar. 30, 2004. Each of these applications is hereby expressly incorporated by reference in their entirety.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

1. Field of the Invention

The present invention relates to improvements in radiation protection. More particularly, the invention relates to the use of silicon particle nano-clusters formed with crystalline cores and amorphous shells that are used for absorbing ultraviolet wavelength radiation in a protection scheme.

2. Description of the Known Art

As will be appreciated by those skilled in the art, silicon nanoparticles are known in various forms. Patents disclosing information relevant to silicon nanoparticles include U.S. Pat. No. 7,078,276, issued to Zurcher, et al. on Jul. 18, 2006; U.S. Pat. No. 7,020,372, issued to Lee, et al. on Mar. 28, 2006; U.S. Pat. No. 7,005,669, issued to Lee on Feb. 28, 2006; U.S. Pat. No. 6,961,499, issued to Lee, et al. on Nov. 1, 2005; U.S. Pat. No. 6,846,565, issued to Korgel, et al. on Jan. 25, 2005; and U.S. Pat. No. 6,268,041, issued to Goldstein on Jul. 31, 2001; U.S. Pat. No. 6,992,298, issued to Nayfeh, et al. on Jan. 31, 2006.

Other publications to consider include:
1. Canham, L. T., Appl. Phys. Lett., 1.990, vol. 57, p. 1046;
2. Klein, K., Sun Products: Protection and Fanning Carol Stream; Allured, 1998, p. 5;
3. Ishchenko, A. A., Storozhenko, P A., Tutorskii, I A., et al, RF Patent 2 227 015, 2003;
4. Zhu, Y, Wang, H., and Ong, P R, Appl. Surf Sci., 2001, vol. 171, p. 44;
5. Roldughin, V I., Usp. Khim., 2003, vol. 72, p. 931;
6. Huang, F.-C., Lee, J.-F, Lee, C. K., and Chao, H. P., Colloids Surf., A, 2004, vol. 239, p. 41;
7. Delerue C., Allan O., Lannu M. // J. Lumin. 1990. V.80. P.65-73;
8. Soni R. K., Fonseca L. F., Resto O., Buzaianu M., Weisz S. Z. II J. Lumin. B. 1999, V.83-84. P.187-191;
9. Altman I. S., Lee D., Chung J. D., Song J., Choi M. II Phys.Rev. B. 2001. V.63. P.161406
10. Knief S., WolfganvonNiessen. //Phys. Rev. B. 1999. V.59. P.12940-12945
11. Tsutomu Shimizu-Iwayama, Takayuki 1-lama, David F. Hole, Ian W. Boyd. // Solid-State Electronics. B. 2001. V.45. P.1487-1494
12. Kuzlmin G. P., Karasev M. E., Khokhlov E M., Kononov N. N., Korovin S. B., Plotnichenko V. G., Polyakov S N., Pustovoy V I. and Tikhonevich 0.V. // Laser Physiks 2000. V.10. P.939-945
13. Beckman D., Beiogorokhov Al., Guseinov Sh. L. lschenko A. A., Storojenko P. A., Tutorskyi 1.A., // Patent RU No. 2227015 Under the application for the invention from 05.06.2003 r.
14. Popov A. P., Kirillin M. Yu., Priezzhev A. V., Lademann J., Hast J.a. Myllyla P. Proc.SPIE, // Optical Diagnostics and Sensing V, B. 2005. V.5702. P.113-122.
15. Marchenko V. M., Koltashev V. V., Lavrishev S. V., Murin D. I., Plotnichenko V.0. //Laser Physics. B. 2000. V.11. P.340-347
16. Matsumoto T., Belogorokhov A. I. Belogorokhova L I., Masumoto '1. //Nanoteclmology. B. 2000 V.11. P.340-347.
17. Belogorokhov A I., Bublik V T., Scerbachev K. D., Parhomenko Yu. N, Makarov V. V., Danilin A. V. //Nucl.Instruments and Methods in Phys.Res. B. 1999, V.147, P.320-326
18. Sahu B. S., Agnihotri O P., Jam S. C., Mertens R. a. Kato I. // Appl.Opt.I B. 1990. V.29. P.3189-3496.
19. Abdyurkhanov 1.M., A~wopxauoB K M., Prusakov B. F., Gorelik V S., Plotnichenko B. G. //Physical metallurgy and heat treatment of metals. 1998. No. 10. C.15-17; and
20. "Handbook of optical Constants of Solids", Ed. by Edward D. Palik, Aead. Press. San Diego 1998, P.1, P.11, P. 561-565, P. 575-579.

Each of these patents and/or publications is hereby expressly incorporated by reference in their entirety. As noted by these disclosures, the prior art is very limited in its teaching and utilization, and an improved nanocrystalline based ultraviolet radiation screen is needed to overcome these limitations.

SUMMARY OF THE INVENTION

The present invention is directed to an improved radiation protection scheme. In accordance with one exemplary embodiment of the present invention, nancrystalline silicon is shown to provide an effective ultraviolet absorption barrier for protection from radiation.

The present invention is directed to the structure of the particles of nanocrystalline silicon synthesized in argon plasma with added oxygen. An amorphous shell composed of silicon oxide is formed on the surface of silicon nanoparticles. The particles form clusters with a fractal structure. The present invention discusses the adsorption of nitrogen on a powder of nanocrystalline silicon at 77 K, and adsorption isotherms obtained for nanocrystalline silicon and nonporous silica adsorbents with identical specific surface areas are compared. The values of surface fractal dimension of powdered nanocrystalline silicon are calculated using the Frenkel-Halsey-Hill equation for multilayer adsorption under the dominant contribution of van der Waals or capillary forces. It is shown that surface fractal dimension is a structure-sensitive parameter characterizing both the morphology of clusters and the structure (roughness) of the surface of particles and their aggregates.

In addition, the present invention discloses the optical properties of an emulsion of nanocomposite materials based on silicon powder. Also provided is the method of creation of a new type of emulsion composite, allowing the control of the spectral structure of transmitted electromagnetic radiation. Two embodiments of silicon powder material, containing SiOx (type 1) and SiOx+SiNx (type 2) depending on conditions, are shown to provide varying effects. The results of FTIR-spectroscopy of powder silicon show the formation of SiO2 and SiOx phases on the surface layer of sample type 1 and the formation of nitride phase on the surface layer of sample type 2. The Raman Spectroscopy investigation of two series of samples provides the determination of the dimensions of nanoparticles and their phase structure in the silicon powders. The Ramen Spectra of samples type 1 and type 2 within the range of 500-600 CM1 demonstrates that the silicon powder is nanocrystalline silicon with dimension of d=10±2 nm for type 1 and d=13±2 nm for type 2. Emulsion composite samples with nanocrystalline silicon are provided and a test run of these materials was performed. The Spectra of optical density as well as the spectra of transmission and diffusive reflection into integrative spheres were measured for both types of samples. It was shown that the samples of type 2 are preferable as the most effective protective ingredients of sunscreens.

These and other objects and advantages of the present invention, along with features of novelty appurtenant thereto, will appear or become apparent by reviewing the following detailed description of the invention.

BRIEF DESCRIPTION OF THE SEVERAL VIEWS OF THE DRAWINGS

In the following drawings, which form a part of the specification and which are to be construed in conjunction therewith, and in which like reference numerals have been employed throughout wherever possible to indicate like parts in the various views.

DETAILED DESCRIPTION OF THE INVENTION

Figure 1:
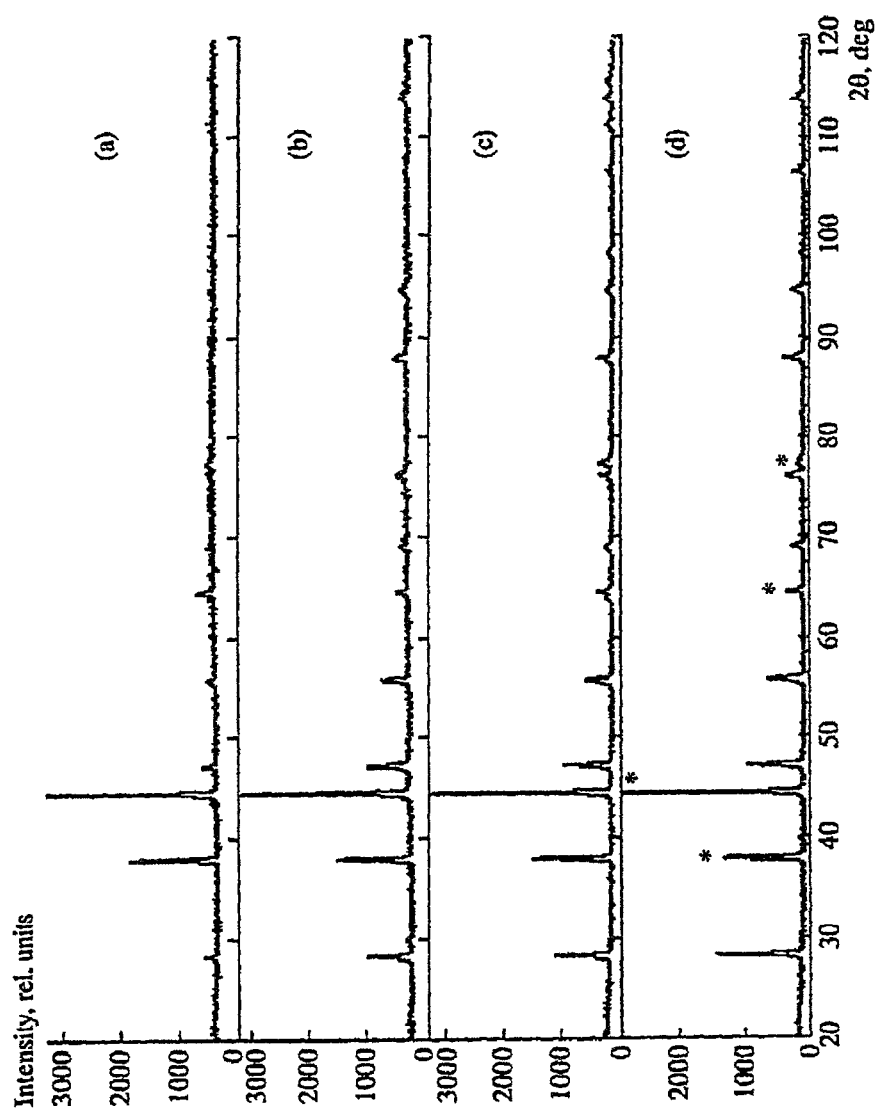
FIG. 1 is an X-ray diffraction pattern of four samples of nanocrystalline silicon with asterisks denoting peaks referred to Al.

First, we take a look at the structure and adsorption properties of nanocrystalline silicon. In recent years, ever increasing interest is caused by nanostructured systems. Nontrivial properties of these systems make it possible to find their unexpected application in diverse objects including the development of new functional elements and composites. The unique properties of nanosized objects are determined mainly by the effect of the surface on atomic and electronic processes at a quantum level. The bulk part of nanocrystals is formed by the initial crystal lattice whose average size is of several tens of nanometers. This size predetermines the region of the localization of wave functions of electrons and holes. For this reason, optical and electron properties of nanocrystals where the motion of charge carriers is limited in two (quantum lines) or three (quantum dots) directions are different than those of their bulk analogs. Among the objects with altered optical properties, the nanocrystalline silicon (NS) is the most attractive substance due to its ability to shift the edge of major absorption to visible and ultraviolet regions.

At present, there are two main classes of complex emulsion media, which are used for the absorption of ultraviolet radiation. In the first class, chemical compounds with chromophore groups absorbing radiation in the UV region are used. In the second class of compounds, strong scattering of photons from the ultradispersed particles of some metal oxides incorporated into the matrix is employed. However, practical application of these media can lead to negative consequences. For example, as was shown in some works, their application as sunblocking materials gives rise to the emergence of melanoma due to the TJV degradation of proteins and the formation of active radicals.

For the development of sunblocking composites, others have proposed to use the physical effect of the UV photon absorption without the reemission of photons with different energy characteristics. These proposal have been limited in their success. However, this effect can be rather simply implemented in the NS particles, because variations in their sizes and surface modification allow us to control their optical properties. In turn, knowledge of the interrelation between the structure of nanosized particles and their optical properties makes it possible to purposefully develop new production technologies of sunblocking composites.

The powdered NS was synthesized in argon plasma in a closed gas cycle. Deep gas cleaning from moisture and oxygen impurities was performed using aluminum melt or special finishing cleaning agents that reversibly absorb impurities up to several parts per billion. The system was filled with argon from the main line. The gas was circulated using a membrane pump. Compressed gas was fed trough the receiver to rotameter ramp and then was redistributed to the blocks of plasma unit. A plasma evaporator-condenser operating in a low-frequency arc discharge was used a reactor. The initial raw material was silicon powder, which was supplied to the reactor by the gas flow from the dosing tank. The powder in the reactor evaporated at 7000-10000° C.

At the outflow from the high-temperature plasma zone, the obtained gas-vapor mixture was subjected to abrupt cooling with the gas jets resulted in the condensation of silicon vapor and formation of an aerosol. The obtained aerosol with temperature of 100-200° C. was fed to the refrigerator where it was cooled to 60-80° C. Large particles, together with unreacted fraction including unprocessed fraction, were separated from the ultradispersed powder in an inertial classifier.

The resultant powder was then collected on a hose-type cloth filter. From the filter, the powder was discharged in an inert atmosphere in a box into a hermetic vessel or was transported to a microencapsulation system where the inert protective layer preventing the powder from ambient effects was deposited onto the powder surface, Photomicrographs were taken with a Fillips EM-301-NED transmission electron microscope at an accelerating voltage of 80 kV. The NS powder was deposited onto a copper grid placed on a carbon substrate.

The X-ray diffraction analysis was performed with a Shimadzu Lab XRD-6000 instrument with $CuK_{\alpha}$ radiation with Ni filter at a current of 20 mA, a voltage of 40 kV, and a scanning rate of 4 deg/min. Equal amounts (about 1.00 mg) of NS powder on the aluminum substrate was placed in a cell and X-ray diffraction patterns were obtained at 2θ angles varying from 20° to 120°.

Isotherms of low-temperature nitrogen adsorption at 77.3 K were measured on a Gravimat-4303 automatic vacuum adsorption unit with a sensitivity of I jig for a sample of 100 mg at a relative pressure varied from 104 to 0.9.

Four NS samples prepared in the induction argon plasma under different conditions were studied. The results of the initial four samples are detailed in the figures and the following detailed discussion.

FIG. 1 shows X-ray diffraction patterns for four NS samples. The degree of crystallinity was calculated by the integral intensity of the most characteristic peak at 2θ=28° assigned to nanocrystalline silicon.

Figure 2:
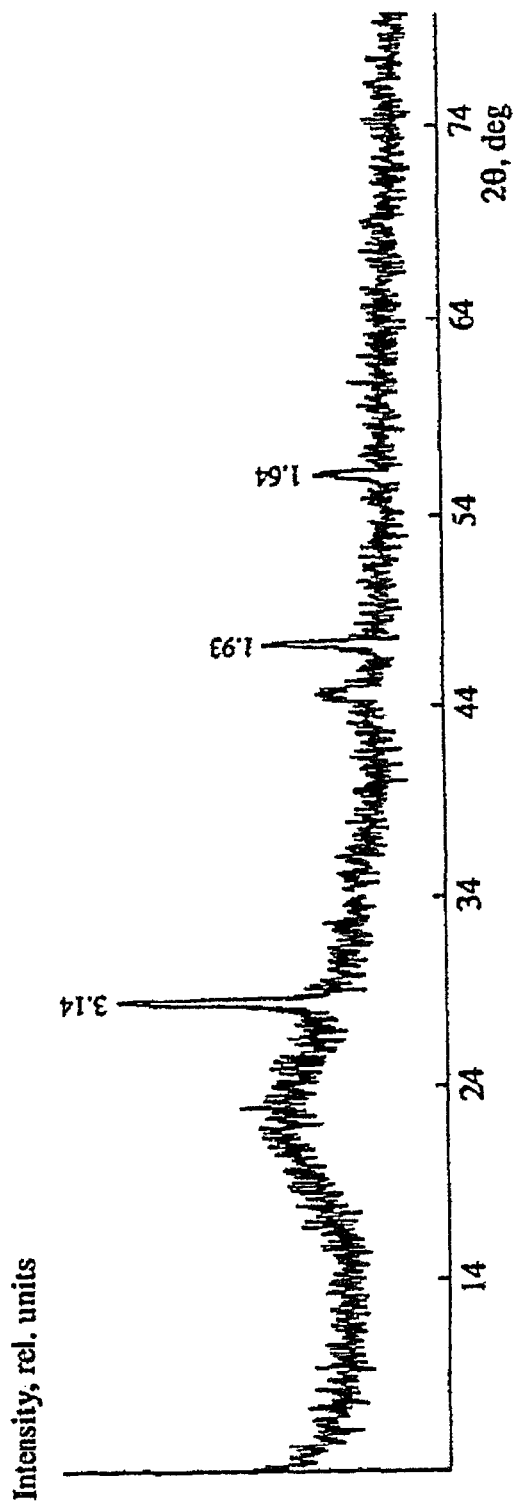
FIG. 2 is an X-ray diffraction pattern of nanocrystalline silicon prepared with atmospheric oxygen.

The diffraction pattern of the first sample prepared under the conditions that allow for the contact between the aerosol and air is presented in FIG. 2. The presence of diffuse scattering halo in the range of 2θ=20°-30° corresponding to amorphous $SiO_2$ indicates the surface oxidation of silicon particles and the formation of particles with the structure of "core-shell" type where the core is the silicon nanocrystal and the shell consists of silicon oxide of various degrees of oxidation. According to this data, the degree of sample crystallinity is ~10%. Relative intensity of the peaks at 2θ=20°-30° corresponding to crystalline silicon for samples 1-4 is arranged in the series 1.0, 3.6, 3.4, and 4.2. Consequently, the degree of crystallinity for the studied samples was 10, 36, 34, and 42%, respectively. As is seen from FIG. 1, the background on the X-ray pattern becomes less intense with an increase in the degree of crystallinity that corresponds to a decrease in the fraction of amorphous phase.

The degree of crystallinity of NS particles characterizes the ratio of the number of atoms forming the crystal core to the number of atoms forming the amorphous shell. These data do not allow us to estimate the shell thickness and the degree of core coverage, i.e., the continuity or mosaicity of a shell. It is also impossible to determine the proportion between silicon with different degrees of oxidation.

Figure 3:
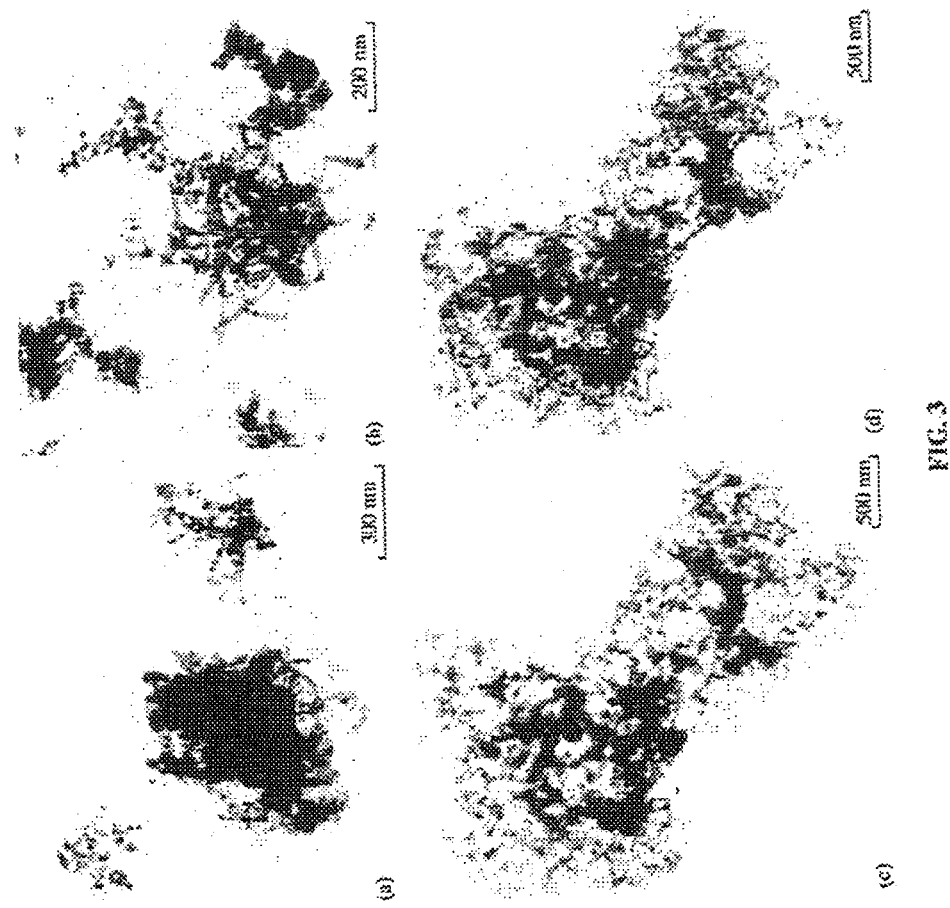
FIG. 3 is electron phtomicrographs of samples (a,b) 1 and (c,d) 2 of nanocrystalline silicon with (c) showing initial observation and (d) showing the after effect of seven minutes of electron beam.

The morphology of NS powder was studied by transmission electron microscopy. FIG. 3 demonstrates the photomicrographs of various NS samples. On photomicrographs, one can distinguish between the branched aggregates (clusters) formed by the particles with sizes of 20-30 nm. The shape of aggregates changed during the observation, thus indicating the aggregate disintegration under the action of electron beam. Local destruction of small aggregates and thinning of chains formed by nanoparticles can be seen in photomicrographs (FIGS. 3c and 3d). The disintegration of aggregates occurs due to the entrainment of silicon atoms or nanoparticles with sizes smaller than 10 nm.

Fractal dimension df of NS aggregates was determined from electron microscopy images using the box-counting method used in the art. The values of fractal dimension were calculated from the aggregate projections.

TABLE 1

|  | Magnification | | |
| --- | --- | --- | --- |
|  | $1 \times 10^5$ | $5 \times 10^4$ | $3.3 \times 10^4$ |
| Sample 1 | 1.72 | 1.82 | 1.79 |
| Sample 2 | 1.68 | 1.70 | 1.67 |

Table 1 shows fractal dimension $d_f$ determined by the projection of powdered NS aggregates at different image magnifications. As is seen from Table 1, there is a satisfactory agreement between the $d_f$ values obtained for the same sample at different magnifications. This is indicative of the hierarchic structure of NS aggregates preserving the fractal structure at various levels, i.e., of the presence of self-similarity as one of the main features of fractal systems.

The coincidence of $d_f$ values for different samples indicates the resemblance of their preparation conditions and the structure of aggregates.

The structurization of powdered NS is determined by the surface properties of a shell composed of silicon oxide with different degrees of oxidation. Surface properties were studied by the technique of low-temperature nitrogen adsorption. This method also makes it possible to draw some conclusion about the morphology of powders and the presence of pores. We performed comparative study of low-temperature nitrogen adsorption on nanocrystalline silicon and different silica adsorbents (silica gels) with known specific surface area and surface structure.

Figure 4:
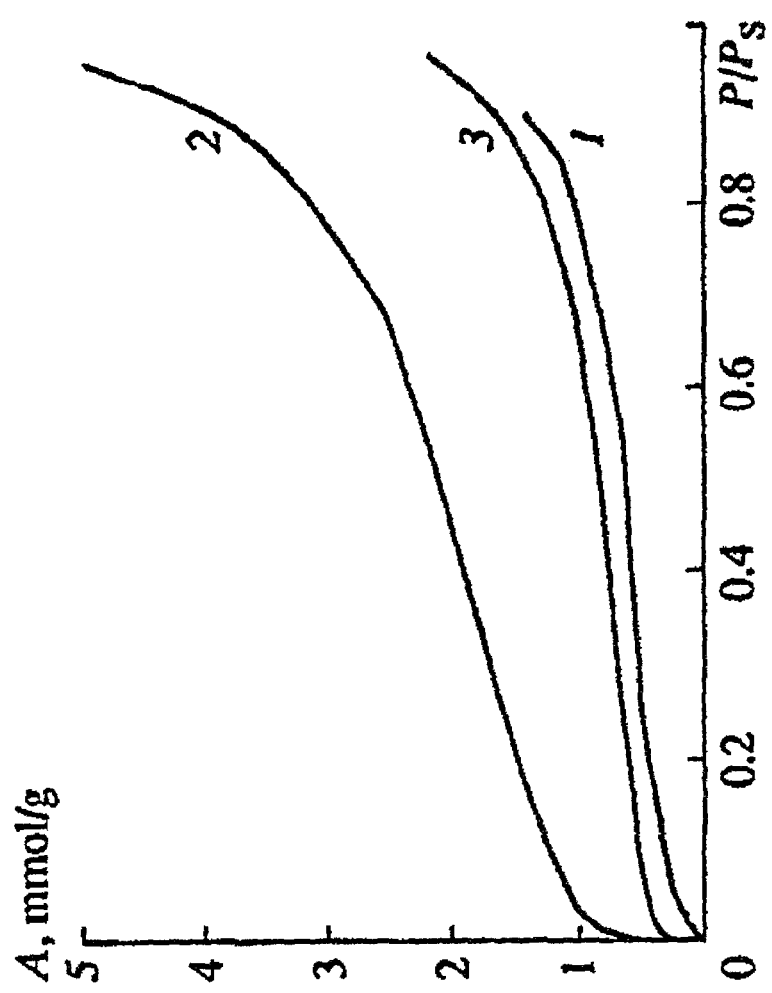
FIG. 4 shows adsorption isotherms of nitrogen at 77.3 k obtained for three different samples of nanocrystalline silicon.

FIG. 4 demonstrates the isotherms of low-temperature nitrogen adsorption on various NS samples. The obtained isotherms belong to type II (according to Brunauer's classification) and are characterized by a large slope in the saturation region with the predominant polymolecular adsorption.

Using obtained isotherms, we calculated the values of specific surface areas by the linearized BET equation and the characteristic energy of adsorption by the Dubinin-Radushkevich equation.

We also compared nitrogen adsorption isotherms for nanocrystalline silicon and nonporous silica adsorbents with similar values of specific surface areas (determined by the BET technique).

Figure 5:
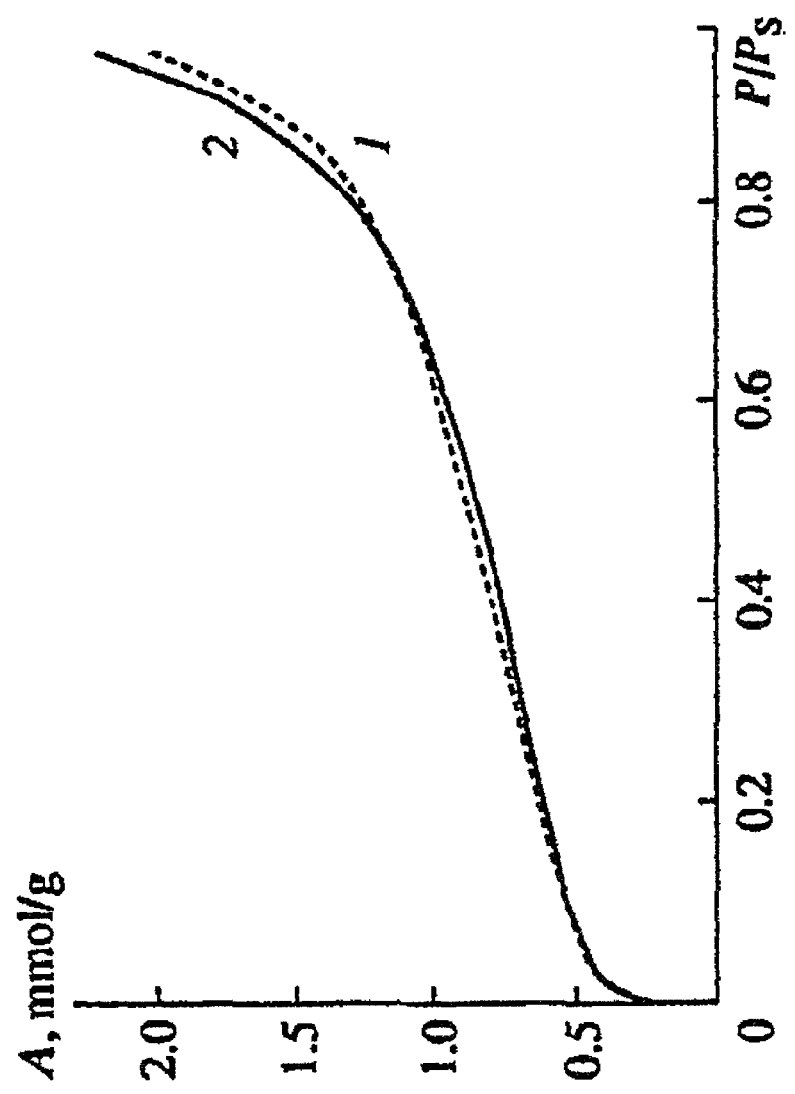
FIG. 5 shows adsorption isotherms of nitrogen at 77.3 k obtained for (1) Aerosil AS-2 and (2) nanocrystalline silicon with specific surface areas of 55 $m^2/g$.
Figure 6:
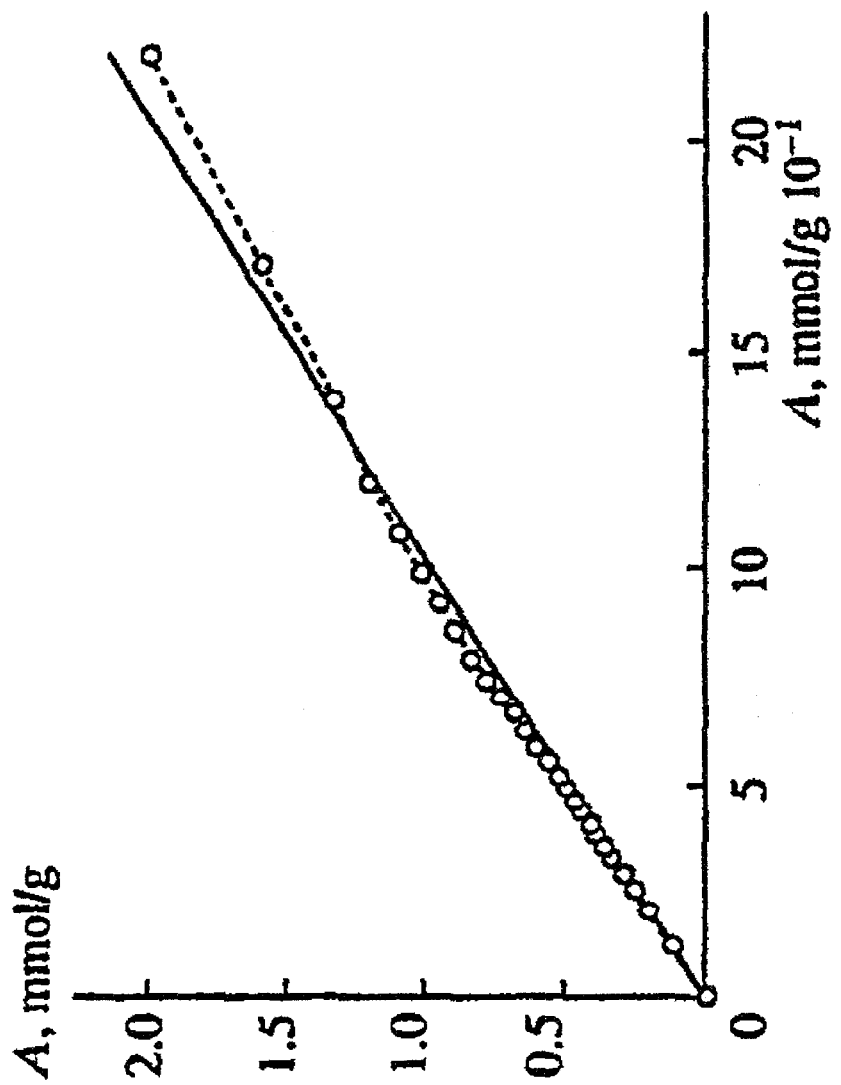
FIG. 6 shows a comparison of adsorption values at identical relative pressures obtained for standard Aerosil AS-2 and NS with specific surface areas of 55 $m^2/g$ with adsorption on NS plotted on the abscissa axis and adsorption on standard Aerosil on the ordinate axis.

FIG. 5 shows the adsorption isotherms for two adsorbents with similar values of specific surface areas: Aerosil with a specific surface area of 55 m2/g (curve 1) and NS with the same value of specific surface area. We also compared the adsorption values at the same relative pressures for these two adsorbents (FIG. 6). The values of adsorption on NS are plotted on the x axis; those on standard Aerosil, on the y axis at the same relative pressures. The value of correlation coefficient (the reliability of linear approximation) appeared to be 0.99.

The coincidence of adsorption properties of NS with specific surface area of 110 m2/g and nonporous silica and silica gel with the same specific surface areas is also quite satisfactory. This means that nanocrystalline silicon is a nonporous adsorbent.

Thus, the specific surface area of adsorbent characterizes neither the surface structure of NS primary particles nor the structure of its aggregates. Therefore, the necessity arises to search for other characteristic of adsorbent which is a structure-sensitive parameter.

For this purpose, we calculated the values of surface fractal dimension of powdered NS using the Frenkel-Halsey-Hill equation for polymolecular adsorption generalized to the case of fractal surfaces.

The equation has the following form:

$$\frac{N}{N_m} \sim \left[ RT \ln \frac{P_s}{P} \right]^{-1/m}$$

where N/Nm is the degree of surface coverage; P and Ps are the equilibrium pressure and the saturated pressure adsorbate vapor, respectively; and m is the slope of the straight line to the ordinate axis.

The pattern of adsorption isotherm for fractal surfaces depends on the prevalence of the type of adsorption forces in the adsorption process. If van der Waals forces acting between the adsorbent and adsorption layer dominate, the value of fractal dimension D of the surface is calculated by equation $$D = 3\left[ 1 - \frac{1}{m} \right]$$

If the dominating forces are the capillary forces determined by the surface tension at the gas-liquid interface, the D value is calculated by equation $$D = 3 - \frac{1}{m}$$

TABLE 2

| | | Surface fractal dim. | |
|---|---|---|---|
| Sample | $S_{sp}$, m$^2$/g | Calculated by Eq. 2 | Calculated by Eq. 3 |
| 1 | 55 | 1.71 | 2.57 |
| 2 | 110 | 1.95 | 2.65 |
| 3 | 60 | 1.85 | 2.62 |

Table 2 shows surface fractal dimensions of NS.

TABLE 3

| No. | Preparation conditions and characteristics | 1 | 2 | 3 | 4 |
|---|---|---|---|---|---|
| 1 | Plasma-forming gas | Ar | Ar | Ar + O$_2$ | N$_2$ |
| 2 | Plasma temperatures, ° C. | 1 × 10$^4$ | 1 × 10$^4$ | — | 7.3 × 10$^3$ |
| 3 | Mean particle size, nm | 18 | 11 | — | 20 |
| 4 | Peak intensity on diffraction pattern | 809 | 2964 | 2749 | 3412 |
| 5 | Degree of crystallinity | 10 | 36 | 34 | 42 |
| 6 | Specific surface area (by BET), m$^2$/g | 55 | 110 | 60 | — |
| 7 | Activation energy of adsorption, kJ/mol | 12.5 | 11.5 | — | — |
| 8 | Fractal dimension over the area, d$_f$ | 1.67 | | 1.78 | — |
| 9 | Surface fractal dimension D at the prevalence of: | | | | |
| | van der Waals forces | 1.71 | 1.95 | 1.85 | — |
| | capillary forces | 2.57 | 2.65 | 2.62 | — |

Table 3 shows the structural and morphological parameters of powdered NS prepared under different conditions.

Figure 7:
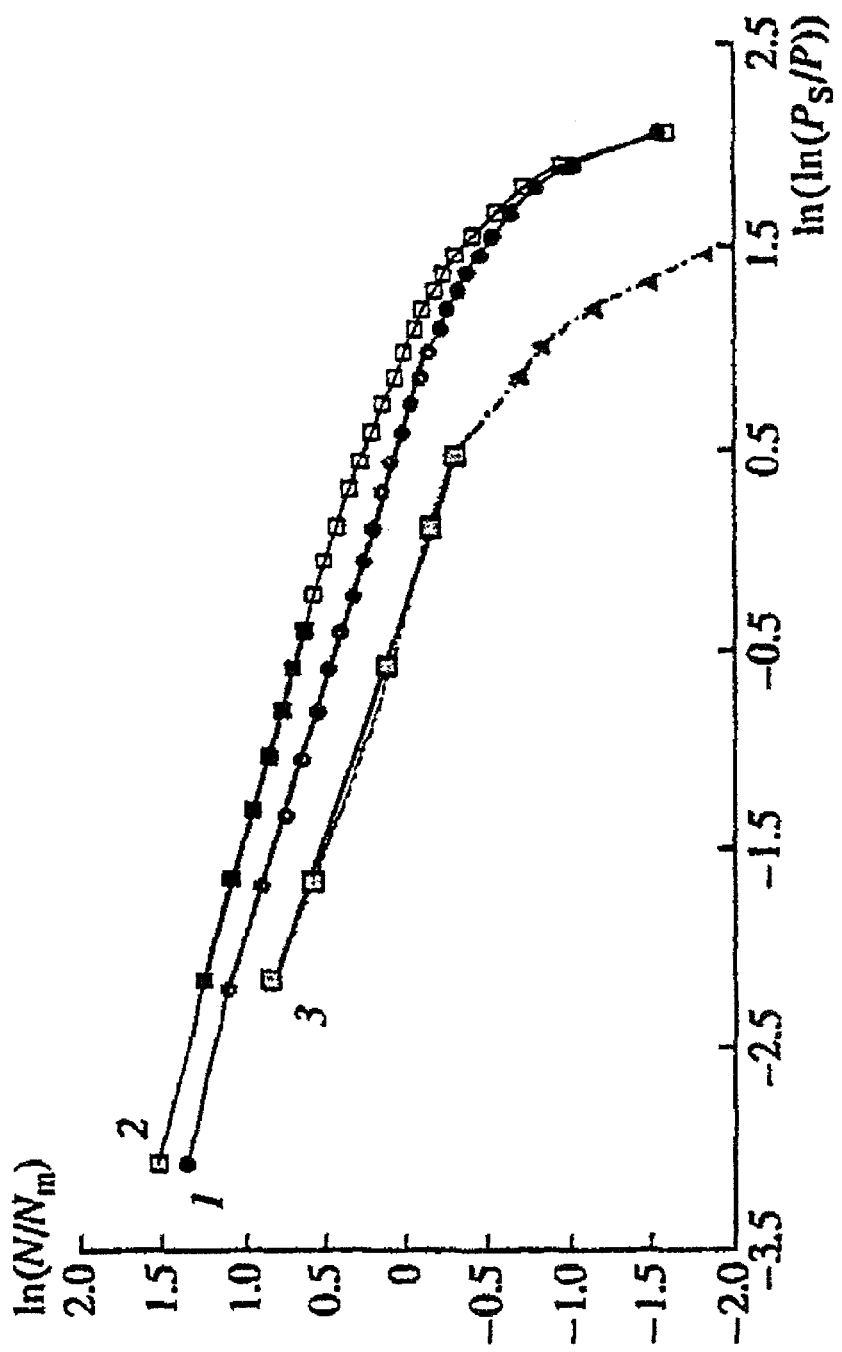
FIG. 7 shows the determination of surface fractal dimensions for three samples of nanocrystalline silicon.

FIG. 7 illustrates experimental dependences in log-log coordinates; Table 2, the values of surface fractal dimension calculated by the linear parts of these dependences and Eqs. (2) and (3). As is seen from these data, the values of surface fractal dimension calculated by the relation corresponding to the prevalence of capillary forces fit interval 2-3.

The values of surface fractal dimension calculated by the relation corresponding to the prevalence of van der Waals forces turned out to be smaller than two, i.e., lower than the value permissible for the rough surfaces. Consequently, the adsorption of nitrogen at 77 K on nanocrystalline silicon within the range of relative pressures of 0.1-0.8 is determined by the capillary forces.

The dependence of structural and morphological parameters of powdered NS on the conditions of powder preparation is shown in Table 3.

Thus, so far we have shown that the combination of X-ray diffraction analysis, transmission electron microscopy, and low-temperature nitrogen adsorption made it possible to establish that, in argon or nitrogen plasma with added oxygen, ultradispersed silicon particles composed of crystalline core and amorphous shell are formed. These particles form fractal clusters whose surface fractal dimension is a structure-sensitive parameter. Surface fractal dimension is an additional quantitative characteristic of various adsorbents and polymer fillers.

Additionally, we consider the unique spectral properties of a nanocomposite material based on silicon Silicon particle nanoclusters, incorporated into various transparent media, are a new object of interest for this physicochemical study. For particles smaller than 4 nm the effects of dimensional quantization are essential, and their use permits control of the luminescent properties and absorbance of materials in UV spectral region. Optical properties of the particles with size of more than ~10 nm are determined mainly by the optical properties of bulk silicon crystals. These characteristics depend on a number of factors such as presence of structure defects, additives, phase state and some other factors.

The plasma technology of silicon powder production in various atmospheres permits verification of the chemical composition of the nanoparticle surface layer. Such ability is not available by ion implantation or radiofrequency precipitation which are the methods ordinarily used for preparation of nanocrystalline silicon.

As far as known to us, detailed study of spectra of composite materials, based on nano sized silicon powder have not been performed before although spectra of nanosized silicon powders, produced by laser-induced decomposition of gasiform SiH4, has been presented.

The creation of new effective UV-radiation protectors, based on silicon nanoparticles is the primary stimulating interest of this applicaiton. A significant advantage of these new materials is their ecological purity. By the changing of nanoparticles size distribution, their concentrations in the composite, and modification of the particle surface, it becomes possible to control spectral characteristics of the nanocomposite material as a whole. For effective protection of human skin, sunscreen ingredients must limit and/or prevent UV transmission within, the range of wavelength less then 400 nm, that define sunscreen properties of commercial creams.

The main goal of this work was the study of spectral properties of oil-water media containing prepared composite silicon nanoparticles with variations in both silicon particle concentration and methods of its production.

Specially prepared highly transparent silicon composite nanoparticles capable of controlling wavelength, transmittance in the range of 200-850 nm, and emulsified as water/oil was used as the base material of samples. The silicon powder was synthesized in a plasmatron in which high-frequency induction plasma interacted with the silicon crystalline samples. Nanoparticle synthesis was performed in an atmosphere of inert gases (He or Ar) with controlled addition of oxygen at the cooling stage of nanoparticle production. The samples of type I were synthesized by this method. The active component of composite is a nucleus of silicon nanocrystals, obtained in oxygen atmosphere. By varying oxygen pressure (rate of oxygen introduction) the surface layer composition and thickness could be changed. The samples of type II were synthesized by adding controlled N2 gas into the atmosphere of oxygen.

The composite emulsions, were prepared by mechanical mixing of the prepared silicon powder types (1 & 2) with oil-water base at a definite mass proportions.

Originally a series of various methods were performed to test silicon powder properties. The method of electronic microscopy (device Philips-EM-300) was used for obtaining the visual imaging of silicon powder particles.

The Fourier infrared spectra were registered using Spectrometer IFS-113v (Bruker) within the range of wave numbers 4000-400 cm-1 with spectral resolution not more then 0.5 cm-1. A thin (~20 µm) layer of the emulsion was located inside special cells between silicon windows.

The Raman spectra were measured using monochromator T-64000 (Yobin Yvon) with excited radiation from argon laser (?=514.5 nm). The CCD-matrix was applied when cooled to 1.40 K for detection of Raman radiation. The bulk silicon crystal was used as the standard. The effect of samples heating under impact of laser radiation, which can essentially change Raman scattering spectrum image, was tested and found to be negligible under our experimental conditions. In the set of experiments the samples were prepared by incorporating the silicon powder into silicate glue. Such techniques provided stable, easy and multiple spectra measurements of the same sample in different experiments.

Spectrophotometer "Specord-M40" (Carl Zeiss, Jena) was used to study spectra of transmission in the 200-850 nm optical range. The spectra measurements were carried out using two different methods. The first one allowed measurement of probe light attenuation in collimated geometry, providing data of optical density. In the second method, the diffuse transmission of the probe light into the integrating sphere was measured. This allowed taking into account the power of radiation that passed through the sample in all directions inside $2\pi$ solid angle. Specifically designed cells with UV quartz windows were used to keep the thickness of investigated emulsions in the range of 10-20 micron.

Figure 8:
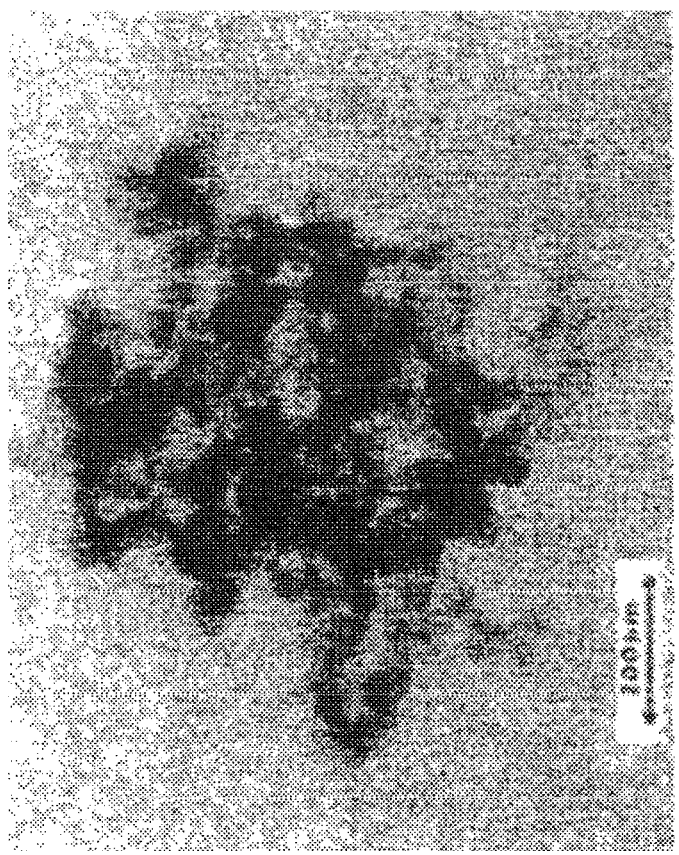
FIG. 8 shows pictures of silicon nanoparticles of type I at magnification.

Next, we take a look at the electron microscopy and infrared spectroscopy of silicon powder. The pictures of silicon nanoparticles of type I, are presented in FIG. 8 at magnification. One can see that the silicon particles generated by plasmatron are complex fractal aggregates with a characteristic size of a few hundred nanometers which consist of a number of smaller particles of more than 10 nm size.

Figure 9:
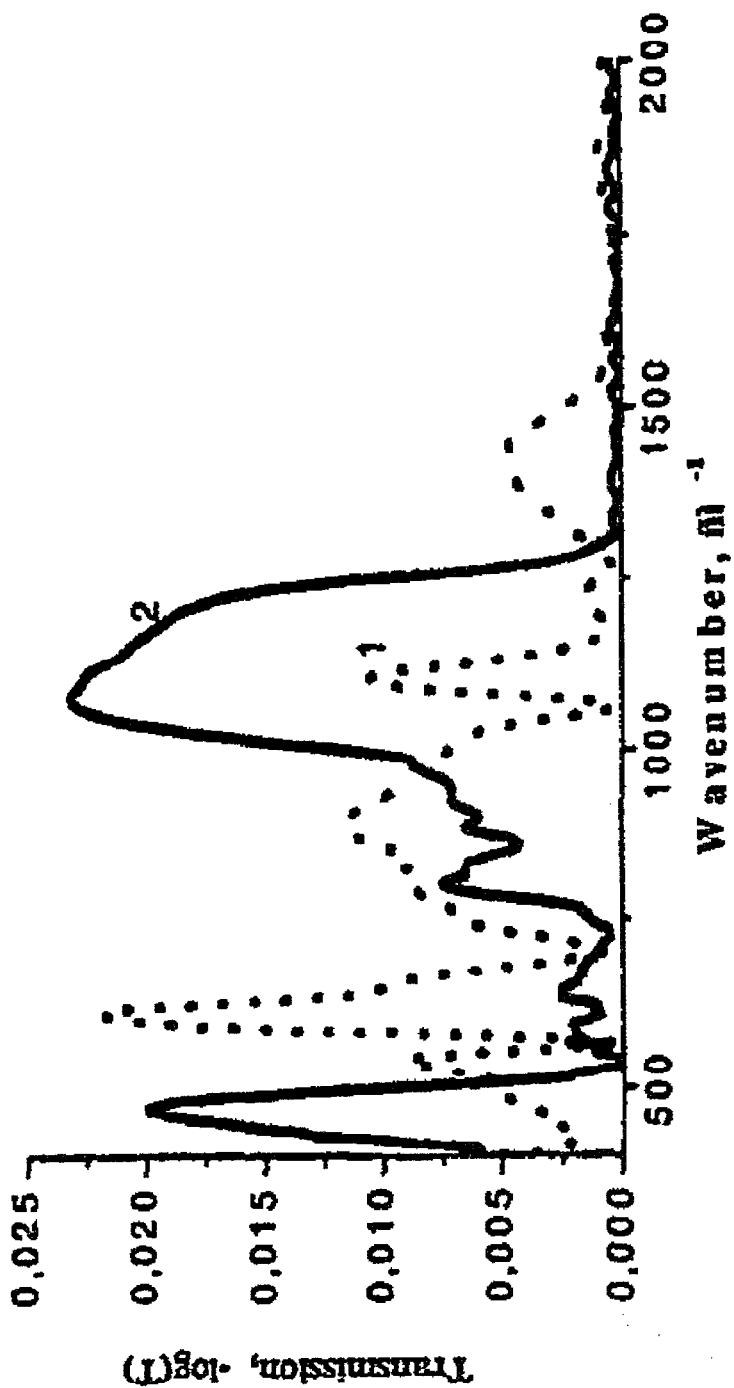
FIG. 9 shows the infrared spectra of samples types I and II.

The infrared spectra of Type I sample revealed an intensive band of absorbance at wave numbers 461, 799, 978, 1072 and 1097 cm-1 (FIG. 9). The appearance of these bands indicates the formation of phases SiO2 or SiOX (x=1.5-2). We assumed these phases are formed on the particle surfaces. The spectra of the particles of Type ii bands at 60, 82, 1190 and 1360 cm-1 revealed additional bands indicating formation of oxynitrogen groups SiXOYNZ. The relation between components of this phase is strongly dependent on the conditions of synthesis.

Figure 10:
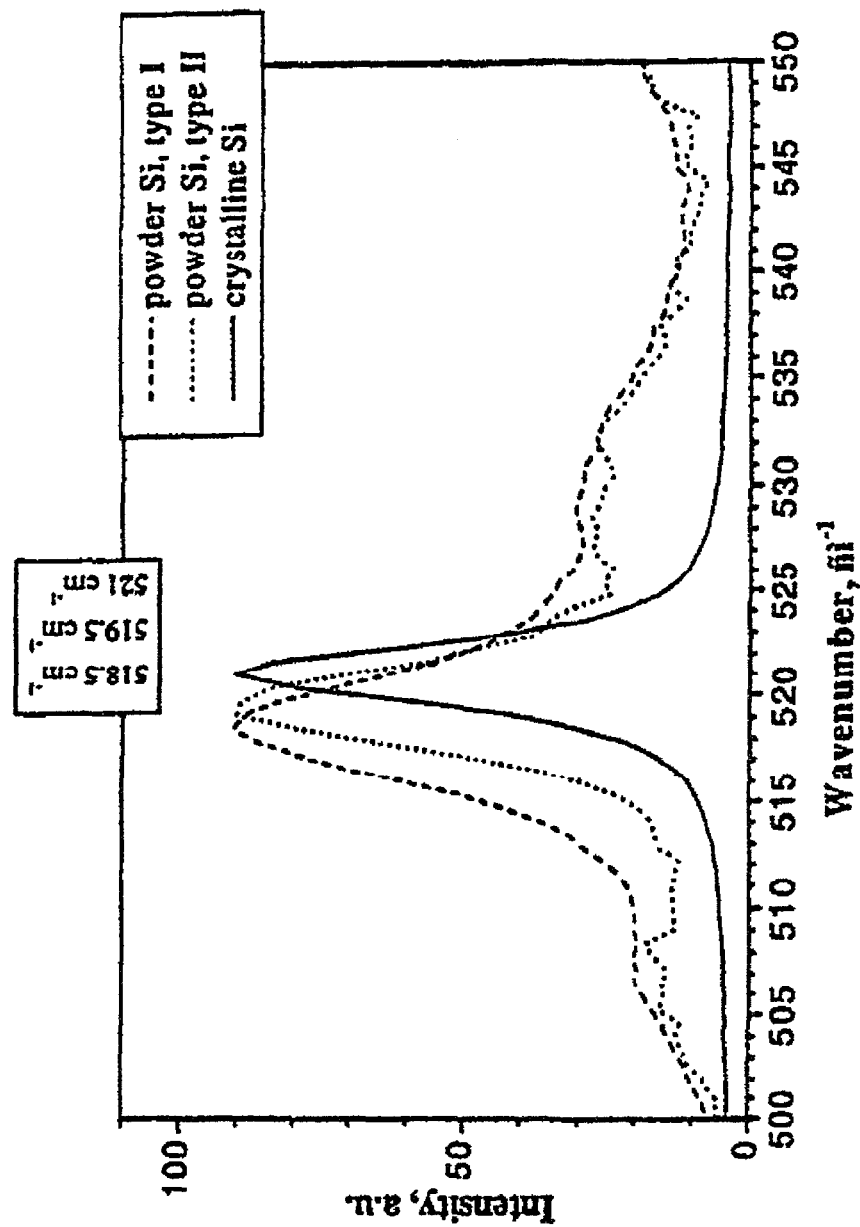
FIG. 10 shows the Raman spectrum of silicon powder incorporated into the matrix of silicate glue (1-2%) as well as the Raman spectrum of crystalline silicon.

FIG. 10 presents Raman spectrum of silicon powder incorporated into the matrix of silicate glue (1-2%) as well as Raman spectrum of crystalline silicon. The influence of glue spectrum bands on the spectra of silicon powder was verified as rather small near the 521 cm-1 peak at appropriate concentrations of silicon powder. The spectral band of silicon crystal is shifted to low frequencies with respect to corresponding bands of both powder samples (types I and II) on about 1.5-2.5 cm-1. Besides, the width of silicon powder peak is about 25% more of that for crystal silicon which is about 4 cm-1. Similar results were also obtained for Raman spectrum of emulsion, containing silicon particles.

The analysis of the Raman spectra shows, that the structure of synthesized silicon powders of types I and II is close to crystalline silicon. In the alternative case of amorphous silicon the width of peak would be a few times more and its maximum would be in the range of 480-490 cm-1.

According to known art, the shift of the Raman bands of silicon powders to low frequency with respect to the band of crystalline silicon is connected with the quantum size effect when the size of silicon particles is decreased to nanometer scale.

To evaluate the size of particle it is possible to use the equation, which relates the shift of Raman band and size of particle (equation 4):

$$\Delta\gamma \cong \frac{S^2}{4c^2\gamma_0 L}$$

where S is the speed of sound in the crystal, c is the speed of light in the crystal, $\gamma_0$ is the wavenumber of Raman band maximum for macroscopic crystal, L is the characteristic size of silicon particle. Using this equation the characteristic sizes of silicon particles were estimated as ~10±2 nm for samples of type I and ~15±2 nm for samples of type II. Note, that the electron microscopy investigations are in well agreement with the data of particle size estimated by Raman spectra analysis. In the conclusion of this section should be pointed that presented evaluations of sizes of nanocrystal particles are quite approximate, because the averaged values of the sound speed in crystal and refraction index within the visible spectrum range were used. The accuracy of size estimation by equation 4 is also decreased if the size of particles increases.

Nevertheless the used approach is defensible. For example, similar estimations of thickness of thin crystalline silicon films well correlated with appropriate measurements by absorbance spectra.

Figure 11:
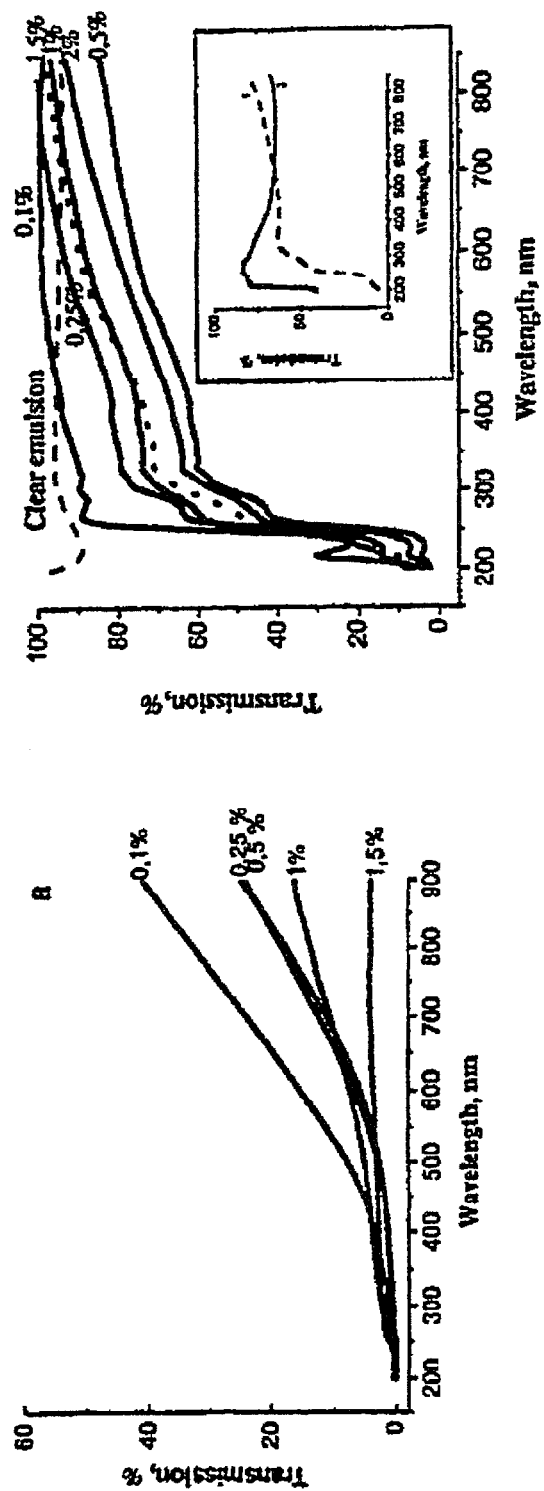
FIG. 11 shows the transmission spectrum T(λ) of emulsions containing nanocrystalline silicon of type I, optical density changing И transmission spectrum into sphere and presenting at the insert the transmission spectrum of the initial sample containing 1% powder Si (1) and after heat treatment at 800° (2).
Figure 12:
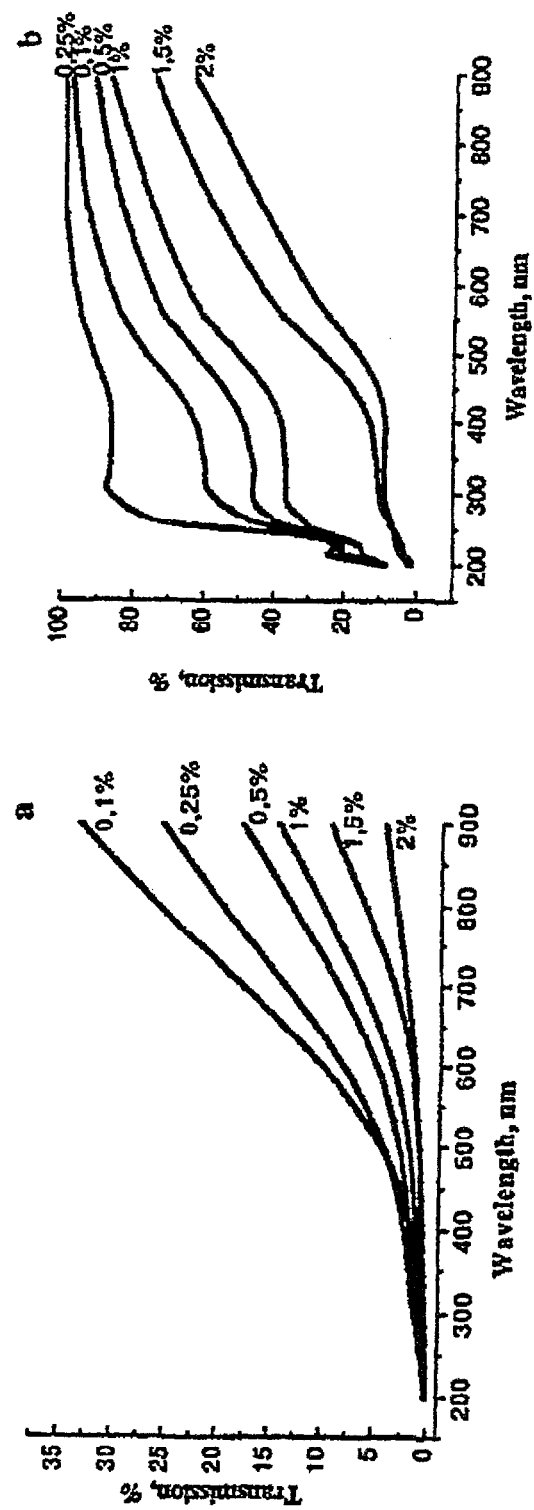
FIG. 12 shows the transmission spectrum of emulsions containing nanocrystalline silicon of type II, optical density changing (a) transmission spectrum into sphere (b).

Transmission spectrum T(λ) of emulsions, containing nanocrystalline silicon, are presented in FIG. 11. These spectra correspond to change of optical density. Each series of spectra was registered for definite sample type with corresponding mass concentrations of silicon powder. To reveal the influence of silicon powder on the composite transmittance we used an oil-water emulsion with high transparency within the entire range of spectrum used. The spectra series for given types of powder revealed some similarities. Namely, the spectra for 0.25 and 0.5% concentrations of silicon powder in emulsion are strongly changing dependencies T(λ), whereas for concentrations of about 1% higher the transmittance is just changed slightly. Maximum light transmittance of an emulsion of 20-micron thickness at 850 nm wavelength is less then 1% for both types of sample. It is important to note that for low concentrations of silicon powder (≤0.5%) the transmittance for the sample of type I increased with the wavelength increase but not for the sample of type II.

Spectral measurements of transmittance were made with the same silicon powder samples using integrating sphere. These measurements permit one to obtain more information about characteristic changing of composite transmission because of taking into account the diffuse scattering into 2π angle. The experiment is of practical interest from the viewpoint of creation of UV light protectors. FIG. 4 shows a quite high transmission signal within whole spectral region, including UV-range 230-400 nm.

The transmission level weakly depends on the concentration of nanocrystalline silicon powder. Maxima within the range of 230, 280, 400 nm on the FIG. 4b, are connected most likely with the absorbance bands of pure base and bands, corresponding to oxide covering and "silicon" nucleus. By increasing the concentration from 0.1 to 2% transmission for type II sample is decreased greatly and becomes lower 7% in the range of 200-450 nm.

Comparing results, presented on the FIG. 4 and FIG. 5, one can conclude, that for nanocrystalline silicon particles of type I the relative contribution of light scattering effects on total transmittance is larger than that for particles of type II, especially in the range of 200-450 nm. Yet for samples of type I the contribution of light absorbance by particles is determinative in UV range. It can be seen especially for large concentrations of particles in emulsion. Taking into account that nanocrystalline particles for samples of both types have similar size of "silicon" nucleus, these differences in transmission spectra are obviously connected to the presence of chemically different surfaces, and therefore with difference of their optical properties.

As known, silicon oxynitrides have too much radiation losses within UV-range compared with silicon oxides. Therefore the effect of light absorption for particles of type II can be determinative in measuring transmission spectra by the integrating sphere due to presence of "oxynitride" covering, assuming the cover is quite thick in comparison with diameter of the particle. But effects of light scattering could be determinative at spectral measuring due to "oxide" covering. The following fact for this can be evidence. The transmittance of emulsion in UV range with silicon powder thermally treated in air during 1 hour at 600-800° is increased (see insert on FIG. 11b). Also the infrared and Raman spectra of those samples indicate the increase of thickness of "oxide" covering and evidently a relative decrease of thickness of the "silicon" nucleus.

In consideration of the mechanism of spectra formation it is necessary to take into account that Fresnel reflection $$R \approx \left(\frac{n-n_0}{n+n_0}\right)^2$$

for "oxide" layer is less of that for "oxynitride" layer, because refraction coefficient n is changed from 1.46 (for SiO2) to 2.0 (for SixOyNz). This circumstance could be kept in mind for more detailed analysis of total light losses using as absorption spectra and the spectra of reflection.

Figure 13:
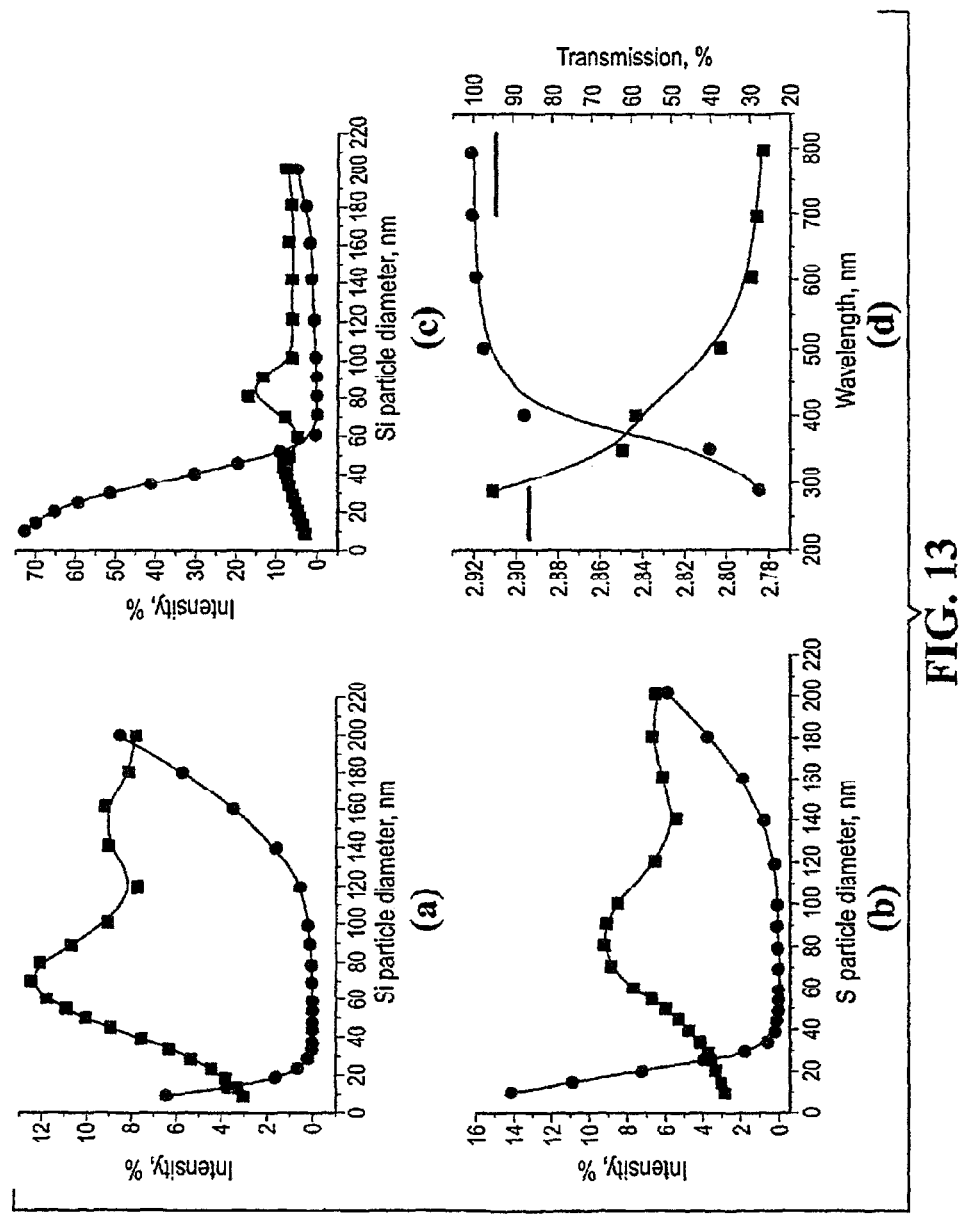
FIG. 13 shows diffuse reflection (squares) and transmission (dots) of Si nanoparticle dredge (including volume fraction 0.5%) within a 20-mkm layer of water-oil media (for incident radiation with wavelength 290 (a), 350 (b) 400 Hm (c)) in dependence of average Si nanoparticle diameter (d) for different wavelength of incident radiation at particle diameter of 10 nm.

In the conclusion of this section consider theoretically the influence of size and concentration of pure silicon nanoparticles on the integrated transmittance and reflectance of the media containing them for various wavelengths. The chosen model parameters are close to the conditions of our experiments: the silicon spherical particles are assumed to be uniformly distributed in nonabsorbing media layer of 20 nm thickness and volume concentration of particles about 0.5% (≈1% mass concentration). The size of particles varied from 10 to a few hundred nanometers. The real and complex parts of refractive index of crystal silicon were taken for wavelengths 290, 350 and 400 nm from previous numbers known I the art while media refractive index was taken $n_0$=1.4 assuming it independent of wavelength. Reflected and transmitted photons were counted into solid angle 2π of appropriate back and straight hemispheres. The Monte-Carlo method based on Mie theory of light scattering was used for calculations. Numerical results of our calculations are presented on FIG. 13. It shows that for given wavelength there exists characteristic dimension of particles providing simultaneously as minimal transmittance and maximal reflectance. Evidently, such correlation is the result of energy balance.

When decreasing of light wavelength this size is shifted to smaller values: 60-90 nm for λ=400 nm, 40-100 nm for λ=350 nm and 25-1.00 nm for λ=250 nm. Note that for particles of minimal size used in our calculations (10 nm) transmittance is decreased quite steeply if the wavelength decreased (see FIG. 13d). Presented dependence appeared more close to the data of sample of type I as a whole.

Thus, the spectral properties of an emulsion containing silicon nanoparticles are shown to be effective UV protectors. Two types of silicon nanoparticles were synthesized by plasmachemical sputtering of bulk silicon crystal with the quenching of generated particles in atmospheres of oxygen and nitrogen. The synthesized silicon nanoparticles were determined by Raman spectroscopy as crystalline with characteristic size of about 1.0-15 nm. This size is well correlated with the data obtained by electron microscopy. Infrared spectroscopy of the samples containing silicon nanoparticles revealed a number of characteristic bands of silicon oxides SiOx (x=1.5-2) and oxynitrogen groups, which presumably formed an envelope of a few nanometer thickness that cover the silicon crystal nucleus. This envelope could essentially influence the scattering and absorption properties of nanoparticles depending on the particles type. Particularly, scattering is more effective for $SiO_x$ coverings while absorption effect is more essential for $Si_xO_yN_z$ coverings.

Theoretical analysis of the integrated by $2\pi$ solid angle transmittance and reflectance of the silicon nanoparticles as a function of their size shows that a minimum of transmittance and a maximum of reflectance are well correlated depending on the particles size and wavelength.

For particles of about 10 nm diameter the transmittance is strongly decreased with the wavelength decrease to UV spectral range.

From the foregoing, it will be seen that this invention well adapted to obtain all the ends and objects herein set forth, together with other advantages which are inherent to the structure. It will also be understood that certain features and subcombinations are of utility and may be employed without reference to other features and subcombinations. This is contemplated by and is within the scope of the claims. Many possible embodiments may be made of the invention without departing from the scope thereof. Therefore, it is to be understood that all matter herein set forth or shown in the accompanying drawings is to be interpreted as illustrative and not in a limiting sense.

When interpreting the claims of this application, method claims may be recognized by the explicit use of the word 'method' in the preamble of the claims and the use of the 'ing' tense of the active word. Method claims should not be interpreted to have particular steps in a particular order unless the claim element specifically refers to a previous element, a previous action, or the result of a previous action. Apparatus claims may be recognized by the use of the word 'apparatus' in the preamble of the claim and should not be interpreted to have 'means plus function language' unless the word 'means' is specifically used in the claim element. The words 'defining,' 'having,' or 'including' should be interpreted as open ended claim language that allows additional elements or structures. Finally, where the claims recite "a" or "a first" element of the equivalent thereof, such claims should be understood to include incorporation of one or more such elements, neither requiring nor excluding two or more such elements.

What is claimed is:

1. An ultraviolet radiation protection composition comprising:
    synthesized silicon nanoparticles having a characteristic size between 1.0 nm and 15 nm formed to have a crystalline core of Si and an amorphous shell of SiOx, where x is greater than 1; and
    a carrier, selected from the carrier group consisting of water and oil, for dispersing the synthesized crystalline silicon nanoparticles;
    wherein the concentration of synthesized silicon nanoparticles in the carrier is sufficient to have a transmittance of less than forty percent across the entirety of the two hundred nanometer to four hundred and twenty nanometer spectrum of the ultraviolet range.

2. The composition of claim 1, wherein:
    the transmittance is less than thirty percent.

3. The composition of claim 1, wherein:
    the transmittance is less than twenty percent.

4. The composition of claim 1, wherein:
    the transmittance is less than ten percent.

5. The composition of claim 1, wherein:
    the transmittance is less than five percent.

6. An ultraviolet radiation protection composition, comprising:
    synthesized silicon nanoparticles having a characteristic size between 1.0 nm and 15 nm formed to have a crystalline core and an amorphous shell wherein the amorphous shell is formed from a stable compound of silicon, oxygen, and nitrogen; and
    a carrier, selected from the carrier group consisting of water and oil for dispersing the synthesized crystalline silicon nanoparticles;
    wherein the concentration of synthesized silicon nanoparticles in the carrier is sufficient to have a transmittance of less than forty percent across the entirety of the two hundred nanometer to four hundred and twenty nanometer spectrum of the ultraviolet range.

7. The composition of claim 6, wherein:
    the transmittance is less than thirty percent.

8. The composition of claim 6, wherein:
    the transmittance is less than twenty percent.

9. The composition of claim 6, wherein:
    the transmittance is less than ten percent.

10. The composition of claim 6, wherein:
    the transmittance is less than five percent.

11. An ultraviolet radiation protection composition, comprising:
    synthesized silicon nanoparticles having a characteristic size between 1.0 nm and 15 nm formed to have a crystalline core and an amorphous shell wherein the amorphous shell is formed from a stable compound of silicon and oxygen; and
    a carrier, selected from the carrier group consisting of water and oil for dispersing the synthesized crystalline silicon nanoparticles;
    wherein the concentration of synthesized silicon nanoparticles in the carrier is sufficient to have a transmittance of less than fifty percent between the three hundred sixty nanometer to nine hundred nanometer spectrum.

12. The composition of claim 11, wherein:
    the transmittance is less than thirty percent.

13. The composition of claim 11, wherein:
    the transmittance is less than twenty percent.

14. The composition of claim 11, wherein:
    the transmittance is less than ten percent.

15. The composition of claim 11, wherein:
    the transmittance is less than five percent.

* * * * *